(12) United States Patent
Kondo

(10) Patent No.: US 8,602,995 B2
(45) Date of Patent: Dec. 10, 2013

(54) ULTRASONIC DIAGNOSTIC APPARATUS

(75) Inventor: Yuji Kondo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 837 days.

(21) Appl. No.: 12/408,148

(22) Filed: Mar. 20, 2009

(65) Prior Publication Data

US 2009/0247873 A1 Oct. 1, 2009

(30) Foreign Application Priority Data

Mar. 26, 2008 (JP) .................... 2008-081546
Sep. 10, 2008 (JP) .................... 2008-231940

(51) Int. Cl.
*A61B 8/00* (2006.01)

(52) U.S. Cl.
USPC .............. 600/443; 600/407; 600/437; 73/602

(58) Field of Classification Search
USPC ......... 600/407, 425, 437, 440, 442, 443, 455, 600/456, 457, 459; 702/28, 48, 124; 73/599, 602, 606, 620
See application file for complete search history.

(56) References Cited

U.S. PATENT DOCUMENTS

| | | | | |
|---|---|---|---|---|
| 4,845,430 A | * | 7/1989 | Nakabayashi | 324/309 |
| 5,001,649 A | * | 3/1991 | Lo et al. | 702/124 |
| 5,349,862 A | * | 9/1994 | Chubachi et al. | 73/602 |
| 6,091,941 A | * | 7/2000 | Moriyama et al. | 455/126 |
| 6,675,111 B2 | * | 1/2004 | Komatsu et al. | 702/45 |
| 7,409,300 B2 | * | 8/2008 | Hishida et al. | 702/45 |
| 2004/0095349 A1 | * | 5/2004 | Bito et al. | 345/440 |
| 2005/0135190 A1 | * | 6/2005 | Katou et al. | 367/99 |
| 2006/0132338 A1 | * | 6/2006 | Katakura et al. | 341/112 |
| 2007/0046540 A1 | * | 3/2007 | Taenzer | 342/442 |
| 2007/0167801 A1 | * | 7/2007 | Webler et al. | 600/459 |
| 2007/0213614 A1 | * | 9/2007 | Suzuki et al. | 600/443 |
| 2007/0225596 A1 | * | 9/2007 | Iustin et al. | 600/424 |

FOREIGN PATENT DOCUMENTS

| | | |
|---|---|---|
| JP | 2004-208859 A | 7/2004 |
| JP | 2006-175006 A | 7/2006 |

* cited by examiner

*Primary Examiner* — Unsu Jung
*Assistant Examiner* — Michael N Fisher
(74) *Attorney, Agent, or Firm* — Sughrue Mion, PLLC

(57) ABSTRACT

According to the ultrasonic diagnostic apparatus of the present invention, even when the received signal indicating the ultrasonic echo from the artifact is weak such as when the artifact such as the puncture needle is positioned diagonally to the ultrasonic beam, the received signal can be subjected to the signal processing to identify the position of the artifact and provide high visibility of the artifact to an examiner. Thus, from whichever direction the puncture needle is inserted into the body, the position of the puncture needle can be properly recognized.

8 Claims, 7 Drawing Sheets

ULTRASONIC DIAGNOSTIC APPARATUS

BACKGROUND OF THE INVENTION

1. Field of the Invention

The present invention relates to an ultrasonic diagnostic apparatus, and more particularly to an ultrasonic diagnostic apparatus for increasing visibility of an artifact such as a puncture needle.

2. Description of the Related Art

An ultrasonic diagnostic apparatus often performs puncture for puncturing a desired site with a cell needle to obtain a tissue sample for cell tissue diagnosis. At this time, the puncture needle is made of metal and is a specular reflector, and thus when an ultrasonic beam is applied diagonally to the puncture needle, sufficient reflection signals cannot be obtained to make it difficult to visualize the puncture needle.

As shown in FIG. 1, an ultrasonic beam entering the puncture needle at an incident angle $\theta i$ is reflected in a direction of $\theta r$, which makes it difficult to detect ultrasonic echoes with an ultrasonic probe. Generally, scattering occurs at an interface in living tissue, and if the beam diagonally enters the interface, most of ultrasonic echoes return to the ultrasonic probe. On the other hand, scattering rarely occurs at the puncture needle having a smooth surface, and minimal echoes return to the ultrasonic probe. As a result, a sufficient signal amplitude for recognizing the puncture needle cannot be obtained. Particularly, the puncture needle is inserted at various angles depending on test areas, and thus the position of the puncture needle sometimes cannot be checked according to conditions, which is clinically extremely inconvenient.

A conventional technique for increasing visibility of a puncture needle is described in Japanese Patent Application Laid-Open No. 2004-208859. An ultrasonic diagnostic apparatus described in Japanese Patent Application Laid-Open No. 2004-208859 mounts a puncture adapter that can detect an insertion angle of a puncture needle to the puncture needle, obtains information on an insertion angle of the puncture needle, determines a position of the puncture needle in a living body from the information on the insertion angle and a luminance signal based on a received signal of a reflected wave of an ultrasonic beam obtained by an ultrasonic probe, identifies a reflection signal from the puncture needle contained in the received signal of the reflected wave of the ultrasonic beam, and enhances the reflection signal.

Japanese Patent Application Laid-Open No. 2006-175006 describes an ultrasonic observation apparatus that enhances an artifact such as a puncture needle inserted into a body of a patient. The ultrasonic observation apparatus described in Japanese Patent Application Laid-Open No. 2006-175006 performs a processing for enhancing the puncture needle on the basis of a correlation value between a waveform obtained on the basis of an ultrasonic echo generated by reflection from a subject and the puncture needle and a waveform of a reference signal obtained from the puncture needle previously measured in water or the like, or a processing for enhancing the puncture needle on the basis of a result of comparison between an amplitude of the waveform obtained on the basis of the ultrasonic echo generated by reflection from the subject and the puncture needle and a predetermined threshold.

SUMMARY OF THE INVENTION

However, the ultrasonic diagnostic apparatus in Japanese Patent Application Laid-Open No. 2004-208859 requires the particular puncture adaptor and further makes control complicated.

For the ultrasonic observation apparatus in Japanese Patent Application Laid-Open No. 2006-175006, when the signal returning from the puncture needle to the probe is weak, the puncture needle is difficult to extract by calculation of the correlation value or a threshold processing, and higher performance than performance of general tomogram display cannot be obtained.

A further conventional technique is to widen an ultrasonic transmitting and receiving opening or emit ultrasonic beams from a plurality of directions to increase an ultrasonic beam entering perpendicularly to a puncture needle. However, the transmitting and receiving opening needs to be limited for increasing resolution in a short distance area, and it is difficult to obtain a beam with an appropriate angle to the puncture needle, while the opening cannot be widened without limitation in a long distance area. For the method of transmitting and receiving ultrasonic beams from a plurality of directions, an image forming method becomes complicated, and the number of frames is generally reduced to reduce time resolution.

The present invention is achieved in view of such circumstances, and has an object to provide an ultrasonic diagnostic apparatus in which even if a received signal indicating an ultrasonic echo from an artifact such as a puncture needle is weak, the received signal can be subjected to a signal processing to identify a position of the artifact and increase visibility of the artifact.

To achieve the object, the ultrasonic diagnostic apparatus according to a first aspect comprises: an ultrasonic probe which applies ultrasonic into a subject so as to take an image of a section including an artifact in a body, and receives an ultrasonic echo reflected from the inside of the subject and the artifact to output a received signal indicating the ultrasonic echo; an orthogonal detection device which orthogonally detects the received signal outputted from the ultrasonic probe; a phase information obtaining device which obtains phase information on the basis of the orthogonally detected signal; a phase difference calculation device which calculates a phase difference indicating a change in the obtained phase information; an artifact extraction device which extracts a characteristic portion of the artifact on the basis of an absolute value of the calculated phase difference; and a first visualization signal processing device which visualizes and outputs the characteristic portion of the extracted artifact.

Sound pressure reflectivity reflection strength of the ultrasonic echo reflected at an interface in entering the artifact from living tissue is positive due to a difference in specific acoustic impedance between the living tissue and the artifact, while the sound pressure reflectivity reflection strength of the ultrasonic echo reflected at an interface in passing through the artifact and again entering the living tissue is negative. For the sound pressure reflectivity reflection strength being positive or negative, the positive strength refers to the same phase (an incident wave and a reflected wave have the same phase), and the negative strength refers to the opposite phases.

The present invention notes the phase change in an area where the artifact exists and extracts the artifact. Specifically, the phase information is obtained from the received signal indicating the ultrasonic echo, and the phase difference indicating the change in the phase information is calculated. The phase difference can be calculated by differentiation of the obtained phase information. Then, the characteristic portion (a phase inverted portion) of the artifact is extracted on the basis of the calculated phase difference, and the characteristic portion of the extracted artifact is visualized and outputted.

As in a second aspect, in the ultrasonic diagnostic apparatus according to the first aspect, the artifact extraction device extracts a portion where the absolute value of the phase difference calculated by the phase difference calculation device becomes a predetermined threshold or higher as a portion containing at least the characteristic portion of the artifact. The portion of the artifact is expected to have a phase difference of 180° in absolute value in principle, but actually does not always have the phase difference of 180° due to the effect of a reflection signal from a deeper portion. However, as compared with other portions having random large phase differences, the portion of the artifact is continuously detected with substantially the same phase difference, and thus an appropriate value can be selected as the threshold to allow a characteristic display of the artifact.

As in a third aspect, in the ultrasonic diagnostic apparatus according to the first or second aspect, the apparatus further comprises a phase difference tomogram generation device which generates a phase difference tomogram on the basis of the absolute value of the calculated phase difference, and the artifact extraction device extracts a portion linearly continuing for a predetermined length or longer in view of a spatial characteristic of the generated phase difference tomogram as a phase difference tomogram of the artifact.

Specifically, the spatial characteristic (for example, a linear shape of the puncture needle) of the artifact is used, and the phase difference tomogram is analyzed to extract the portion of the artifact.

As in a fourth aspect, in the ultrasonic diagnostic apparatus according to any of the first to third aspects, the apparatus further comprises: an amplitude information obtaining device which obtains amplitude information on the basis of the signal orthogonally detected by the orthogonal detection device; an amplitude tomogram generation device which generates an amplitude tomogram on the basis of the obtained amplitude information; a second visualization signal processing device which visualizes and outputs the generated amplitude tomogram; and an image synthesizing device which synthesizes the image of the characteristic portion of the artifact visualized by the first visualization signal processing device and the amplitude tomogram visualized by the second visualization signal processing device.

Thus, the image of the artifact can be displayed so as to be superimposed on the amplitude tomogram (B mode tomogram), thereby increasing visibility of the artifact.

As in a fifth aspect, in the ultrasonic diagnostic apparatus according to any of the first to fourth aspects, the artifact is at least one of a puncture needle, various clips implanted into a body, markers, stents and implants.

According to the present invention, even when the received signal indicating the ultrasonic echo from the artifact is weak such as when the artifact such as the puncture needle is positioned diagonally to the ultrasonic beam, the received signal can be subjected to the signal processing to identify the position of the artifact and provide high visibility of the artifact to an operator. Thus, for example, from whichever direction the puncture needle is inserted into the body, the position of the puncture needle can be properly recognized.

DETAILED DESCRIPTION OF THE PREFERRED EMBODIMENTS

Now, a preferred embodiment of an ultrasonic diagnostic apparatus according to the present invention will be described with reference to the accompanying drawings.

<The Principle Of The Present Invention>

First, the principle of the present invention will be described.

Ultrasonic reflection occurs at an interface between media having different specific acoustic impedances $Z=\rho c$, where $\rho$ is the density of a medium and c is the speed of sound. Sound pressure reflectivity reflection strength Pr of ultrasonic when the ultrasonic enters from a medium 1 to a medium 2 is expressed by the following formula:

$$Pr = (Z_2 - Z_1)/(Z_1 + Z_2)$$ [Formula 1]

where $Z_1$ and $Z_2$ are specific acoustic impedances of the media 1 and 2.

Specifically, a reflection signal is proportional to the difference in specific acoustic impedance between the media. There is a large difference in specific acoustic impedance between a puncture needle of metal and living tissue, and thus the reflection strength is likely to be high.

Figure 1:
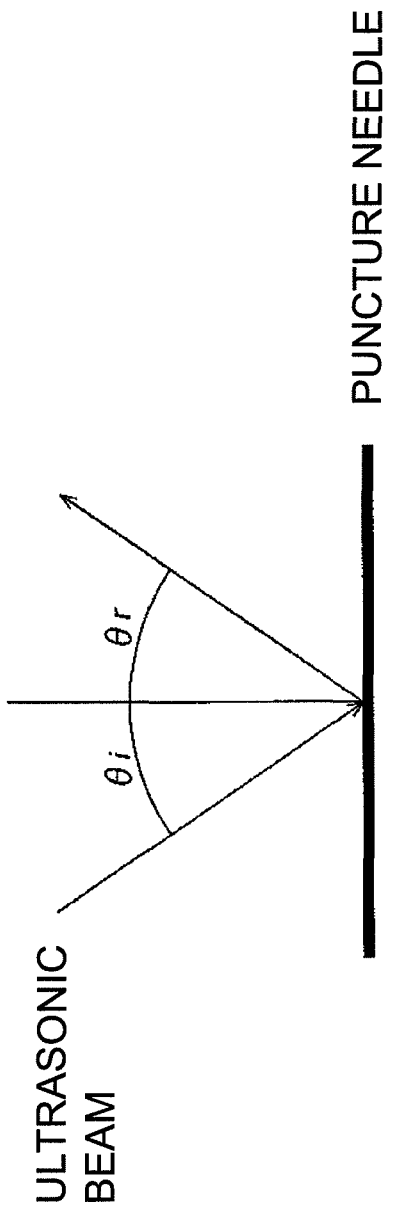
FIG. 1 shows an example of an incident angle and a reflection angle of an ultrasonic beam to a puncture needle.
Figure 2:
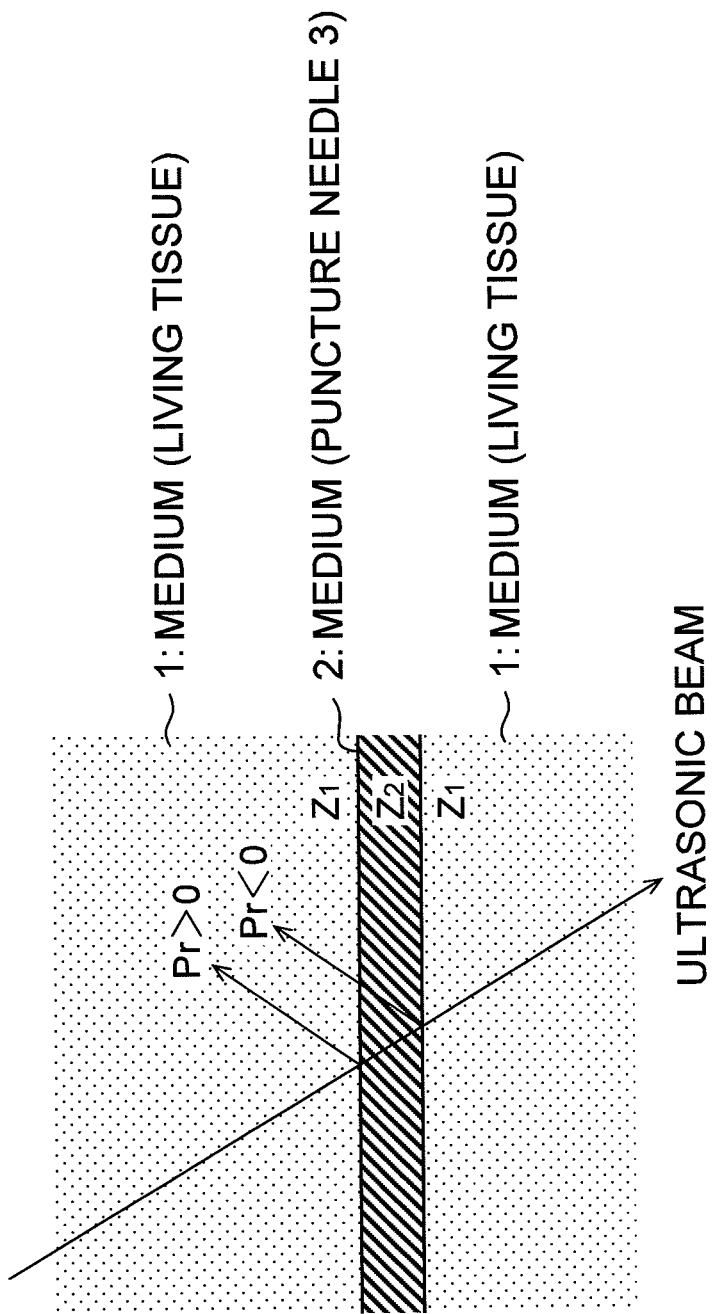
FIG. 2 illustrates a phase of an ultrasonic echo being inverted at an interface between living tissue and the puncture needle.

As shown in FIG. 2, the puncture needle 3 (medium 2) is inserted into the living tissue (medium 1) and an ultrasonic beam is caused to enter, and thus the ultrasonic beam is reflected at an interface in entering the medium 2 from the medium 1, and reflected at an interface in passing through the medium 2 and entering the medium 1 from the medium 2.

As expressed in Formula 1, the sound pressure reflectivity reflection strength Pr of an ultrasonic echo reflected at the interface in entering the puncture needle from the living tissue is positive due to the difference in specific acoustic impedance between the living tissue and the puncture needle, while the sound pressure reflectivity reflection strength Pr of the ultrasonic echo reflected at the interface in passing through the puncture needle and again entering the living tissue is negative. For the sound pressure reflectivity reflection strength being positive or negative, the positive strength refers to the same phase (an incident wave and a reflected wave have the same phase), and the negative strength refers to the opposite phases. Specifically, in an area where the puncture needle exists, a phase of the ultrasonic echo is inverted, and a large phase difference appears (the phase difference of 180° in absolute value if calculated). The area where such a large phase difference appears (that is, an area where the absolute value of the phase difference is a predetermined threshold or more) can be calculated to determine the existence of the puncture needle.

There are various acoustic impedances in the living tissue, and thus there are some areas where the phase difference value is 180° other than the area where the puncture needle exists in various positions. Thus, the area where the phase difference value of 180° is concentrated, particularly the area where the phase difference value linearly continues in view of a shape characteristic of the puncture needle is searched, and thus the area can be determined to be the puncture needle with sufficient grounds. At this time, even if the signal amplitude is not sufficiently higher than in tissue around the area, the phase reflects the situation of the reflector with a slight reflection signal. Thus, the puncture needle can be determined irrespective of existence of images by amplitude strength.

The present invention notes the phase change of the ultrasonic echo in the area where the puncture needle exists, and can satisfactorily extracts the puncture needle even when the received signal indicating the ultrasonic echo from the puncture needle is weak.

<Embodiment Of Ultrasonic Diagnostic Apparatus>

Figure 3:
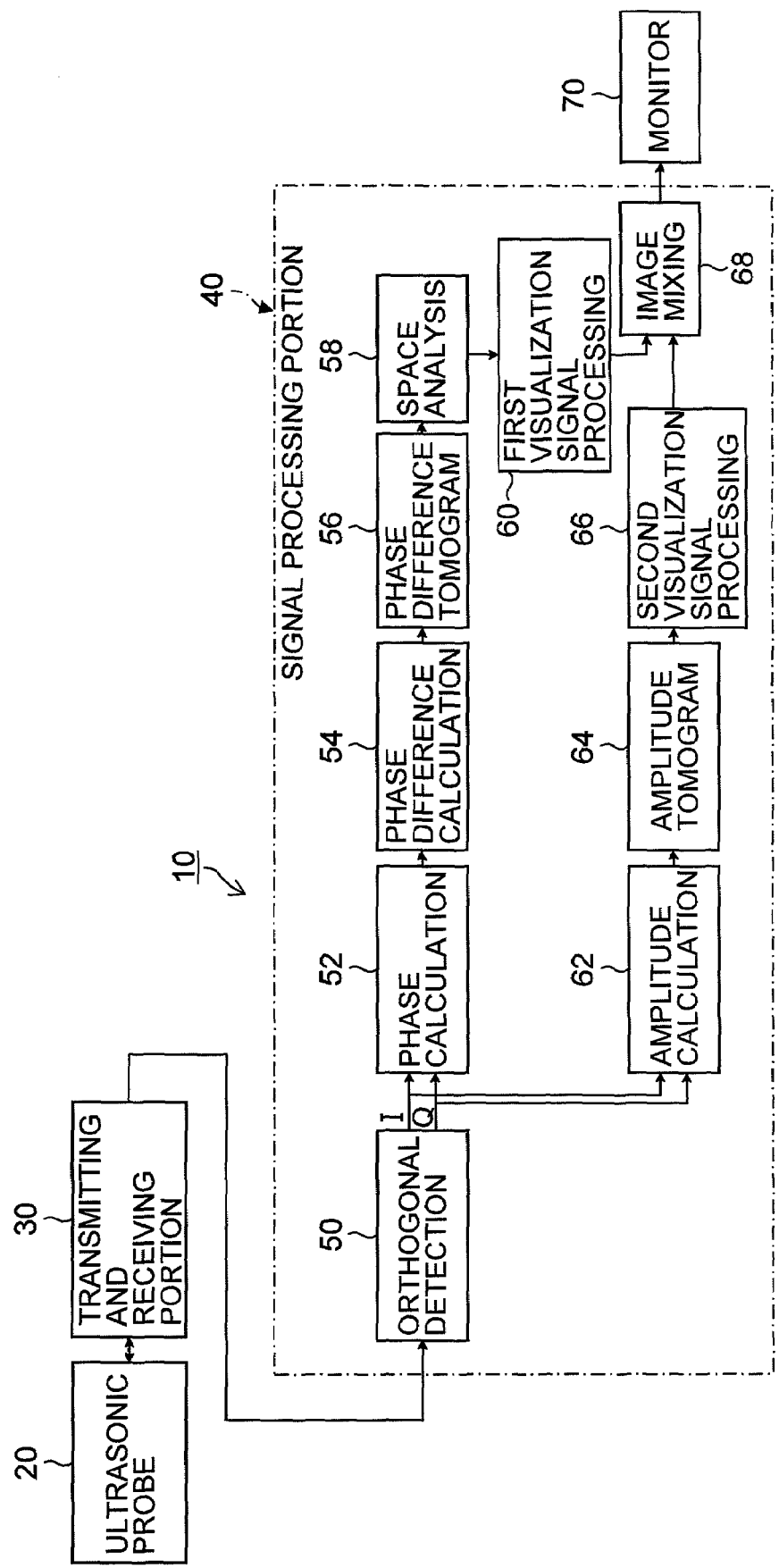
FIG. 3 is a block diagram of an embodiment of an ultrasonic diagnostic apparatus according to the present invention.

FIG. 3 is a block diagram of the embodiment of the ultrasonic diagnostic apparatus according to the present invention.

As shown in FIG. 3, the ultrasonic diagnostic apparatus 10 mainly includes an ultrasonic probe 20, a transmitting and receiving portion 30, a signal processing portion 40, and a monitor apparatus 70.

The ultrasonic probe 20 transmits ultrasonic to a site to be diagnosed in a body of a subject, and receives ultrasonic echoes reflected in the body. The ultrasonic probe 20 in the embodiment includes a plurality of ultrasonic transducers that constitute a one-dimensional ultrasonic transducer array, and each ultrasonic transducer is constituted by an oscillator having electrodes formed at opposite ends of a piezoelectric element such as PZT. The electrode is connected to the transmitting and receiving portion 30 by a signal wire.

The ultrasonic diagnostic apparatus 10 according to the embodiment is used for supporting puncture for puncturing a desired site of the subject with the puncture needle to obtain a tissue sample (visualizing the puncture needle and the desired site), and thus the ultrasonic probe 20 is operated so as to apply an ultrasonic beam to the site to be diagnosed including the desired puncture site.

The transmitting and receiving portion 30 applies an ultrasonic transmission pulse to each electrode of the ultrasonic probe 20, and causes the ultrasonic probe 20 to generate ultrasonic. The ultrasonic probe 20 receives the ultrasonic echo reflected in the body and generates an electric signal, and outputs the signal as a received signal to the transmitting and receiving portion 30. The received signal received by the transmitting and receiving portion 30 is amplified and A/D converted, and then output to the signal processing portion 40.

The signal processing portion 40 includes an orthogonal detection circuit 50, a phase calculation circuit 52, a phase difference calculation circuit 54, a phase difference tomogram generation circuit 56, a space analysis circuit 58, a first visualization signal processing circuit 60, an amplitude calculation circuit 62, an amplitude tomogram generation circuit 64, a second visualization signal processing circuit 66, and image mixing circuit 68.

The orthogonal detection circuit 50 is a circuit that uses a reference signal to orthogonally detect the received signal inputted from the transmitting and receiving portion 30, and divides the received signal into a real number component (cos component) and an imaginary number component (sin component) by the orthogonal detection.

When a waveform y(t) of the received signal is expressed by the following formula:

$$y(t)=u(t)\cos(\omega t+\phi)$$ [Formula 2]

(where u(t) is amplitude and φ is phase)

the orthogonal detection circuit 50 divides the signal into the real number component (cos component) and the imaginary number component (sin component) expressed by the following formula:

$$I=u(t)\cos(\phi)$$ [Formula 3]

$$Q=u(t)\sin(\phi)$$

The real number component is also referred to as an I-component, and the imaginary number component is also referred to as a Q-component.

The phase calculation circuit 52 calculates the phase φ from the I-component and the Q-component added from the orthogonal detection circuit 50 by the following formula:

$$\phi=\tan^{-1}(Q/I)$$ [Formula 4]

On the other hand, the amplitude calculation circuit 62 calculates the amplitude u(t) from the I-component and the Q-component added from the orthogonal detection circuit 50 by the following formula:

$$u(t)=\sqrt{(I^2+Q^2)}$$ [Formula 5]

The phase difference calculation circuit 54 calculates a difference in a depth direction of a phase φθ of the received signal calculated by the phase calculation circuit 52 as required, and for example, can be constituted by a differentiating circuit that differentiates a signal indicating the phase φθ. When the sound pressure reflectivity reflection strength Pr of the received signal is positive, a phase difference calculation output is low, and when Pr is negative, the phase difference calculation output is high around ±180°.

The phase difference tomogram generation circuit 56 converts phase difference information in a scanning space of the ultrasonic beam calculated by the phase difference calculation circuit 54 into phase difference information in a physical space (a section of the site to be diagnosed), and luminance conversion corresponding to the phase difference information (0°-180° to 180° in absolute value) is performed to generate a phase difference tomogram in the section of the site to be diagnosed.

The space analysis circuit 58 is an image processing portion that detects an image portion matching the characteristic of the puncture needle from the phase difference tomogram, and performs, for example, the following processings. First, a portion with an absolute value of a phase difference higher than a preset threshold is extracted to binarize the phase difference information (a phase difference image). The portion with the phase difference higher than the threshold is regarded as a detection point, and an arbitrary detection point is noted, which is regarded as an initial detection point.

Next, an area around the initial detection point is searched to check the presence of a detection point. If there is no detection point around the initial detection point, the initial detection point is abandoned. When there is a detection point therearound, the detection point is regarded as a second detection point, and an angle of a line connecting the initial detection point and the second detection point is calculated. Next, it is checked whether there is a further detection point in a direction of the calculated angle from the second detection point. If there is a detection point, the operation is continued, and when the detection point continues to a preset length, a path of the detection point is estimated as the puncture needle. Specifically, the space analysis circuit 58 estimates the puncture needle using a characteristic amount that the puncture needle has a portion linearly continuing to a predetermined length or longer. The predetermined length may be 4 to 5 mm.

The first visualization signal processing circuit 60 performs display conversion (gradation conversion or color conversion) for displaying the path of the puncture needle estimated as described above with high visibility, and outputs the information as an image signal to the image mixing circuit 68.

The amplitude tomogram generation circuit 64 converts the amplitude information (u(t) in Formula 5) in the scanning space of the ultrasonic beam calculated by the amplitude calculation circuit 62 into the amplitude information in the physical space (the section of the site to be diagnosed), performs a logarithmic amplification processing or correction of attenuation by a distance according to a depth of a reflection position of the ultrasonic beam, and generates an amplitude tomogram (B mode tomogram) in the section of the site to be diagnosed.

The second visualization signal processing circuit 66 performs luminance conversion of the information of the amplitude tomogram inputted from the amplitude tomogram generation circuit 64, and outputs the information as an image signal to the image mixing circuit 68.

The image mixing circuit 68 synthesizes the image signals added from the first visualization signal processing circuit 60 and the second visualization signal processing circuit 66, and superimposes an image of the puncture needle on the B mode tomogram.

The image signal synthesized by the image mixing circuit 68 is outputted to the monitor apparatus 70, where a synthesized image including the image of the puncture needle superimposed on the B mode tomogram is displayed.

When the ultrasonic diagnostic apparatus 10 having the above described configuration is used to operate the puncture needle, the ultrasonic probe 20 is first operated so as to apply the ultrasonic beam to a section including an insertion path of the puncture needle (that is, the site to be diagnosed including a desired puncture site), and the B mode tomogram is displayed on the monitor apparatus 70.

Then, the puncture needle is operated so that a tip of the puncture needle reaches the desired puncture site while the puncture needle is checked on a screen of the monitor apparatus 70.

At this time, even if the puncture needle is inserted diagonally to the ultrasonic beam (even if the received signal indicating the ultrasonic echo from the puncture needle is weak), the received signal is subjected to a signal processing to display the image of the puncture needle so as to be superimposed on the B mode tomogram, and thus the position of the puncture needle in the living tissue can be properly recognized.

EXAMPLE

A puncture needle was inserted into a phantom, an ultrasonic beam was diagonally applied to the puncture needle, and a general B mode tomogram (a conventional B mode tomogram), a phase tomogram, a phase difference tomogram, and a B mode tomogram on which an image of the puncture needle was superimposed were generated.

Comparative Example 1

Figure 4:
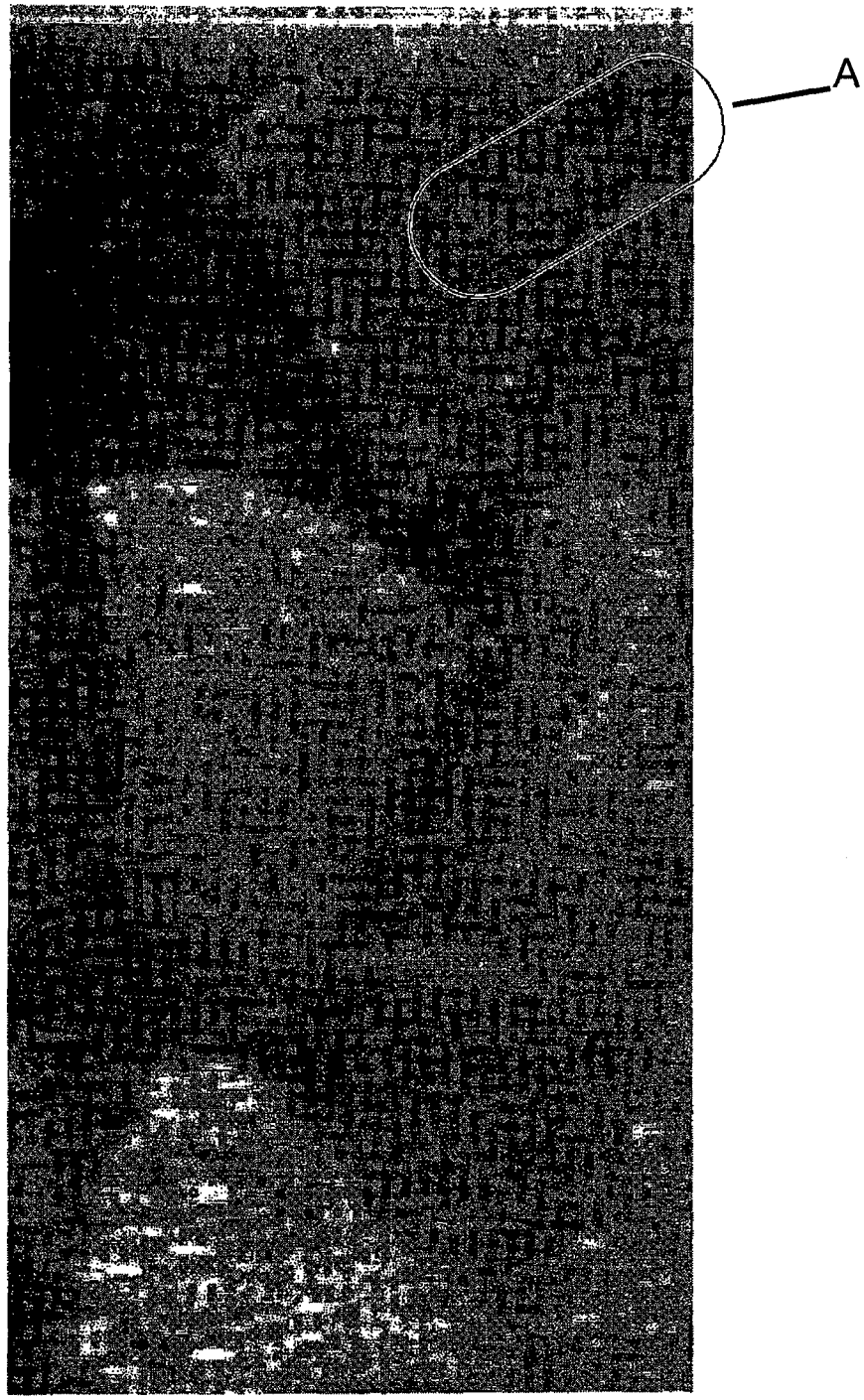
FIG. 4 shows a general B mode tomogram when the puncture needle is inserted into a phantom.

FIG. 4 shows the general B mode tomogram when the puncture needle is inserted into the phantom. In this image, the puncture needle is inserted diagonally to a direction of the ultrasonic beam (vertically to the sheet surface), and thus sufficient signal strength cannot be obtained, and visibility of the puncture needle is extremely low.

Comparative Example 2

Figure 5:
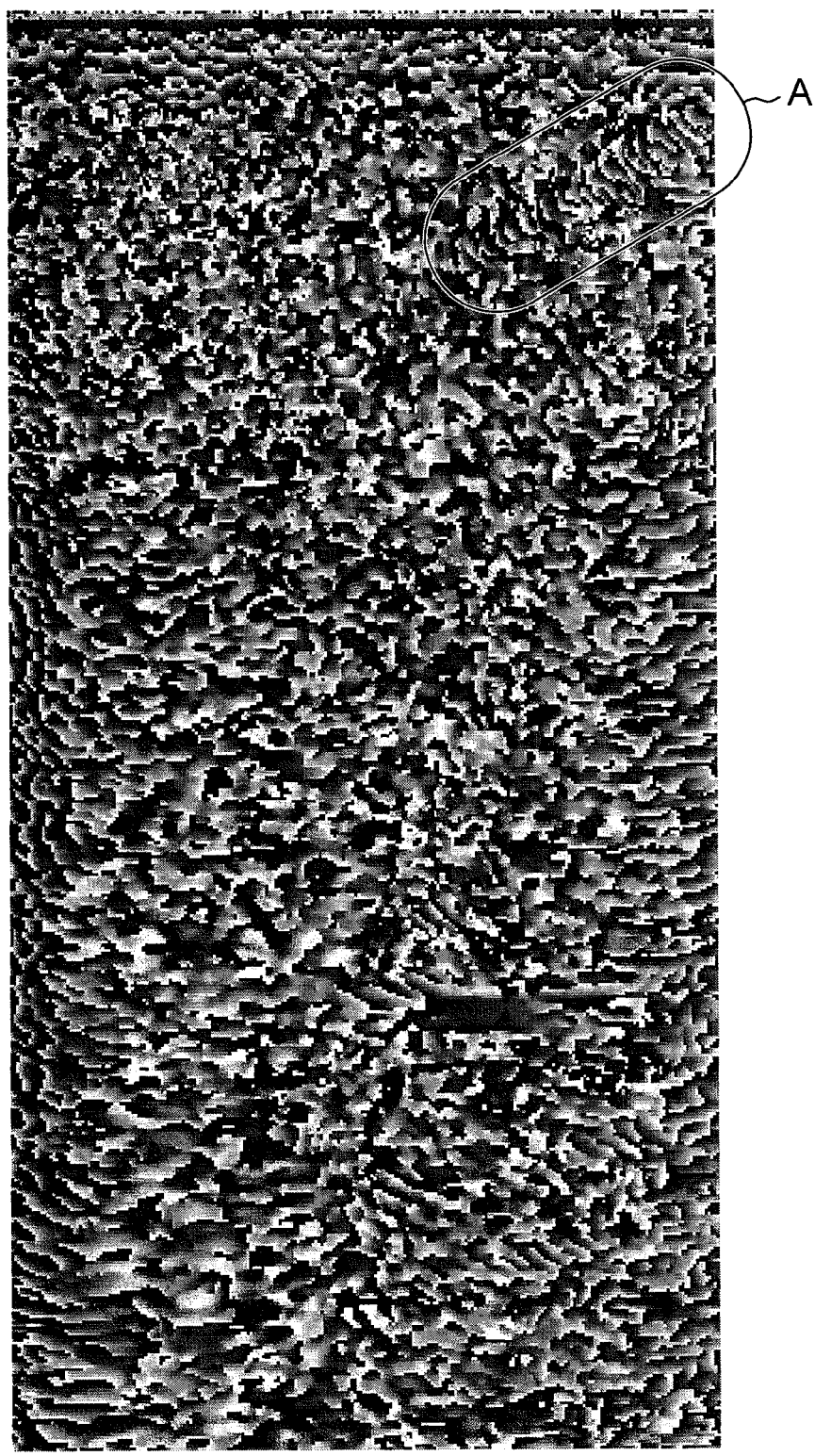
FIG. 5 shows an example of phase information of a received signal in FIG. 4 being visualized as it is.

FIG. 5 shows an example of phase information of a received signal in FIG. 4 being visualized as it is. The phase information is displayed with different luminance according to phases from −180° to 180°. The phase changes at a portion A of the puncture needle, but the phase value itself changes according to the position, and thus it is difficult to identify the position of the puncture needle from the phase value itself.

Comparative Example 3

Figure 6:
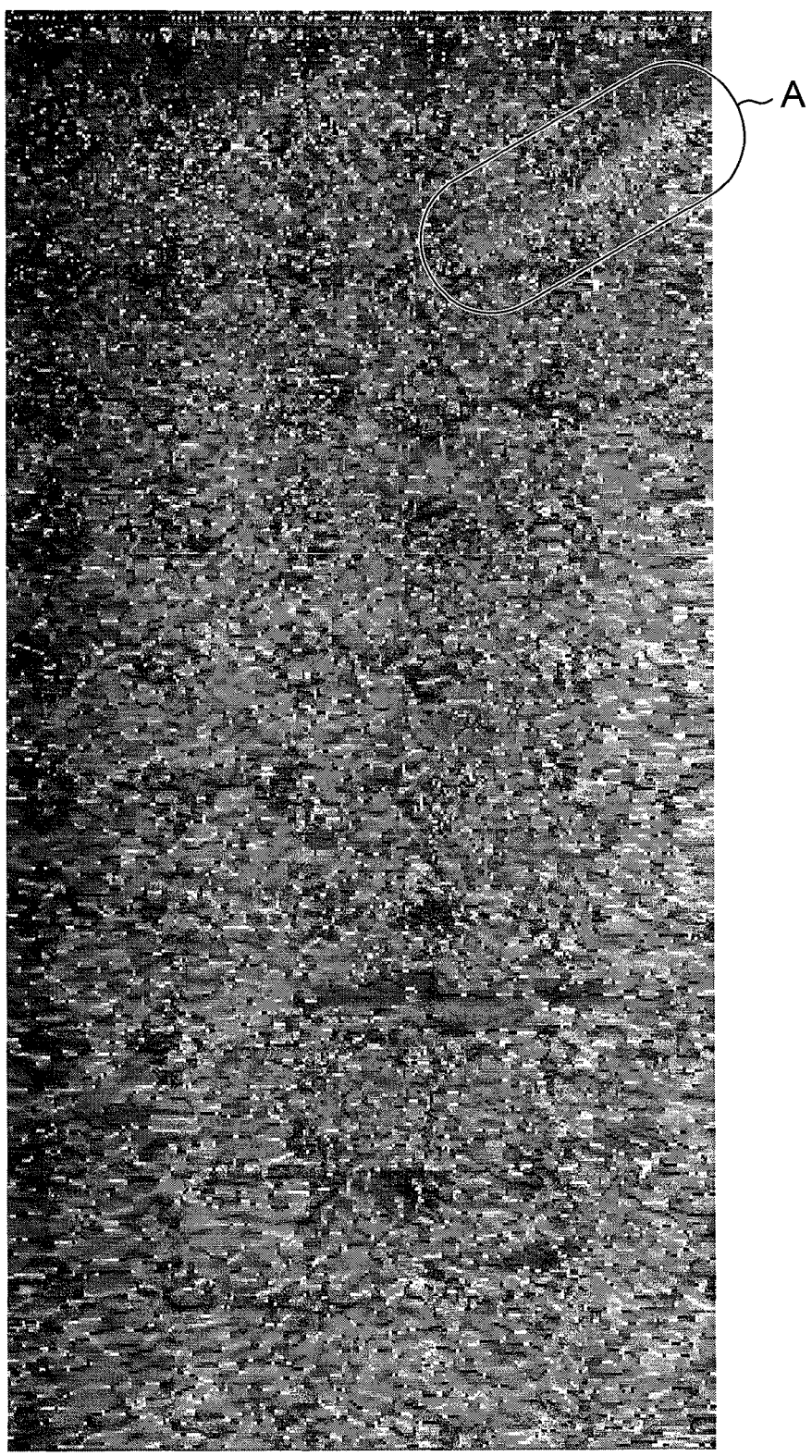
FIG. 6 shows a phase difference tomogram of the phase information in FIG. 5 being subjected to difference operation in a depth direction and visualized.

FIG. 6 shows a phase difference tomogram of the phase information in FIG. 5 being subjected to difference operation and visualized. The portion A of the puncture needle is expected to have a phase difference of 180° in absolute value in principle, but actually does not always have the phase difference of 180° due to the effect of a reflection signal from a deeper portion. However, it can be confirmed that as compared with other portions having random large phase differences, the portion of the puncture needle is continuously detected with substantially the same phase difference to allow a characteristic display of the puncture needle.

In the actual situation, it cannot be always expected to obtain the phase difference of 180° due to the reflection signal from other portions or noise. Thus, realistic determination of phase inversion is performed with a certain threshold being set. The difference value may be replaced by a differential value if phase detection can be continuously performed. Further, it is supposed that in an actual living body, there are reflection sources that cause phase inversion in various positions as shown in FIG. 6. Thus, it is sometimes inconvenient to identify all portions with a large phase difference as shown in FIG. 6 as the puncture needle. In this case, the puncture needle exists substantially linearly, and thus it is effective that an area where a portion having a larger phase difference than a certain threshold exists spatially linearly is extracted by image analysis, and the area is recognized as the puncture needle.

Comparative Example 4

Figure 7:
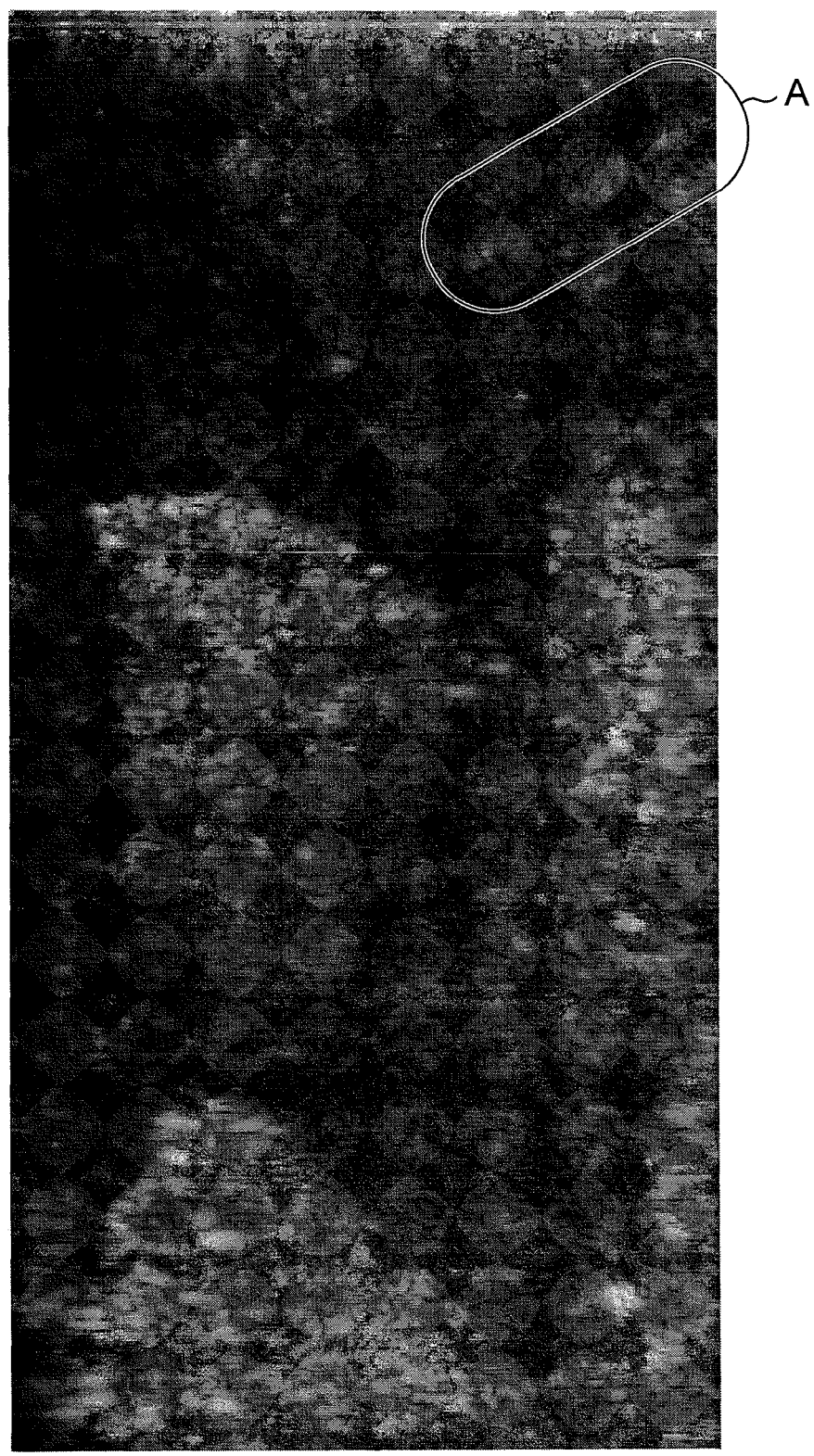
FIG. 7 shows the image information in FIG. 6 being subjected to a proper threshold processing and then displayed so as to be superimposed on the B mode tomogram in FIG. 4.

FIG. 7 shows the image information in FIG. 6 being subjected to a proper threshold processing and then displayed so as to be superimposed on the B mode tomogram in FIG. 4. In FIG. 7, the puncture needle which is unclear in FIG. 4 is clearly drawn, and it can be found that the visibility of the puncture needle is extremely satisfactorily increased.

<Other Embodiment>

In this embodiment, the image of the puncture needle is superimposed on the B mode tomogram, but not limited to this, an image may be generated that is subjected to a processing for extracting a characteristic portion of the puncture needle such as the threshold processing from the phase difference tomogram, and may be displayed separately from or in parallel with the B mode tomogram (synthesized into one screen).

The image processing for extracting the puncture needle from the phase difference tomogram is not limited to the processing in the embodiment, but various methods can be supposed such as calculating a point where the phase difference is within a predetermined range from the initial detection point as a second detection point without binarizing the phase difference information, or a filter processing for detecting a characteristic amount of the puncture needle on the phase difference tomogram. Further, when the puncture needle is identified on the phase difference tomogram, it may be checked by an image processing whether the puncture needle can be identified on the same position on the B mode tomogram or the phase image.

In the embodiment, the puncture needle is described as an example of an artifact, but not limited to this, visibility of artifacts such as various clips implanted into a body, markers, stents and implants for checking the position in surgery can be increased. At this time, a predetermined threshold of the absolute value of the phase difference may be individually set according to the artifacts. Further, as the spatial characteristic amount of the phase difference tomogram, characteristic amounts based on the shapes of the artifacts may be individually adopted.

Further, it is understood that the present invention is not limited to the above described examples, but various changes or modifications may be made without departing from the gist of the present invention.

What is claimed is:

1. An ultrasonic diagnostic apparatus comprising:
    an ultrasonic probe configured to apply an ultrasonic pulse into a subject so as to take an image of a section including an artifact therein, and configured to receive an ultrasonic echo reflected from the inside of the subject and the artifact to output a received signal indicating the ultrasonic echo;
    an orthogonal detection device configured to orthogonally detect the received signal outputted from the ultrasonic probe, and configured to calculate a real number component I ($I=u(t)\cos(\phi)$) and an imaginary number component Q ($Q=u(t)\sin(\phi)$);
    a phase information calculation device configured to calculate a phase $\phi$ ($\phi=\tan^{-1}(Q/I)$) of the received signal from the real number component I and the imaginary number component Q of the orthogonally detected signal;
    a phase difference calculation device configured to calculate a phase difference indicating a change of the phase of the received signal;
    an artifact extraction device configured to extract a characteristic portion of the artifact with an absolute value of the phase difference higher than a predetermined threshold; and
    a first visualization signal processing device configured to perform display conversion to the characteristic portion of the artifact, and configured to output an image signal thereof.

2. The ultrasonic diagnostic apparatus according to claim 1, further comprising
    a phase difference tomogram generation device configured to generate a phase difference tomogram on the basis of the absolute value of the phase difference, wherein
    the artifact extraction device is further configured to extract a linear portion longer than a predetermined length on the phase difference tomogram.

3. The ultrasonic diagnostic apparatus according to claim 1, further comprising:
    an amplitude calculation device configured to calculate an amplitude of the received signal from the orthogonally detected signal;
    an amplitude tomogram generation device configured to generate an amplitude tomogram on the basis of the amplitude of the received signal;
    a second visualization signal processing device configured to perform display conversion to the amplitude tomogram and outputs an image signal thereof; and
    an image synthesizing device configured to synthesize the image signal of the characteristic portion of the artifact outputted from the first visualization signal processing device and the image signal of the amplitude tomogram outputted from the second visualization signal processing device.

4. The ultrasonic diagnostic apparatus according to claim 1, wherein the artifact is at least one of a puncture needle, a clip, a marker, a stent and an implant.

5. The ultrasonic diagnostic apparatus according to claim 1, wherein
    the phase difference calculation device is further configured to calculate the phase difference by differentiating the phase of the received signal in a depth direction of the subject.

6. The ultrasonic diagnostic apparatus according to claim 5, further comprising
    a phase difference tomogram generation device configured to generate a phase difference tomogram on the basis of the absolute value of the phase difference, wherein
    the artifact extraction device is further configured to extract a linear portion longer than a predetermined length on the phase difference tomogram.

7. The ultrasonic diagnostic apparatus according to claim 5, further comprising:
    an amplitude calculation device configured to calculate and amplitude of the received signal from the orthogonally detected signal;
    an amplitude tomogram generation device configured to generate an amplitude tomogram on the basis of the amplitude of the received signal;
    a second visualization signal processing device configured to perform display conversion to the amplitude tomogram and outputs an image signal thereof; and
    an image synthesizing device configured to synthesize the image signal of the characteristic portion of the artifact outputted from the first visualization signal processing device and the image signal of the amplitude tomogram outputted from the second visualization signal processing device.

8. The ultrasonic diagnostic apparatus according to claim 5, wherein the artifact is at least one of a puncture needle, a clip, a marker, a stent and an implant.

* * * * *